(12) United States Patent
Freed et al.

(10) Patent No.: US 10,345,481 B2
(45) Date of Patent: Jul. 9, 2019

(54) ASPHALTENE GRADIENT MODELING METHODS

(71) Applicant: Schlumberger Technology Corporation, Sugar Land, TX (US)

(72) Inventors: Denise E. Freed, Newton Highlands, MA (US); Oliver C. Mullins, Houston, TX (US); Youxiang Zuo, Burnaby (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 768 days.

(21) Appl. No.: 14/571,660

(22) Filed: Dec. 16, 2014

(65) Prior Publication Data

US 2015/0185360 A1  Jul. 2, 2015

Related U.S. Application Data

(60) Provisional application No. 61/921,680, filed on Dec. 30, 2013.

(51) Int. Cl.
| | | |
|---|---|---|
| G01V 11/00 | (2006.01) | |
| G01V 99/00 | (2009.01) | |
| G06F 17/50 | (2006.01) | |
| E21B 43/00 | (2006.01) | |
| E21B 49/08 | (2006.01) | |
| G01N 33/28 | (2006.01) | |

(52) U.S. Cl.
CPC .......... G01V 99/005 (2013.01); E21B 43/00 (2013.01); E21B 49/087 (2013.01); G01N 33/2823 (2013.01); G01V 11/00 (2013.01); G06F 17/5009 (2013.01)

(58) Field of Classification Search
CPC ........ E21B 49/10; E21B 43/00; E21B 49/087; G01V 99/005; G01V 11/00; G06F 17/5009; G01N 33/2823
USPC ...................................................... 703/10, 1
See application file for complete search history.

(56) References Cited

U.S. PATENT DOCUMENTS

| | | |
|---|---|---|
| 4,994,671 A | 2/1991 | Safinya et al. |
| 5,331,156 A | 7/1994 | Hines et al. |
| 6,476,384 B1 | 11/2002 | Mullins et al. |

(Continued)

FOREIGN PATENT DOCUMENTS

WO  2012042397 A2  4/2012

OTHER PUBLICATIONS

Zuo, Freed, Mullins, Zhang ."DFA Profiling of Oil Columns with Asphaltene Grading." SPE Annual Technical Conference and Exhibition. Society of Petroleum Engineers, 2010. pp. 1-10.*

(Continued)

*Primary Examiner* — Kamini S Shah
*Assistant Examiner* — John E Johansen
(74) *Attorney, Agent, or Firm* — Michael Dae (57) ABSTRACT

The present disclosure relates to methods and systems for developing an equation of state model for petroleum fluids. In one embodiment, formation fluid from a plurality of depths within a wellbore may be analyzed to determine a change in a gas oil ratio with respect to depth. The change in the gas oil ratio may be employed to determine a ratio of solubility and entropy terms to a gravity term. The resulting ratio can be used to develop the equation of state model.

20 Claims, 5 Drawing Sheets

(56) References Cited

U.S. PATENT DOCUMENTS

| | | |
|---|---|---|
| 7,526,953 B2 | 5/2009 | Goodwin et al. |
| 7,822,554 B2 | 10/2010 | Zuo et al. |
| 7,920,970 B2 | 4/2011 | Zuo et al. |
| 7,996,154 B2 | 8/2011 | Zuo et al. |
| 8,271,248 B2 | 9/2012 | Pomerantz et al. |
| 8,434,356 B2 | 5/2013 | Hsu et al. |
| 8,805,617 B2 | 8/2014 | Zuo et al. |
| 2008/0066904 A1* | 3/2008 | Van Hal ................ E21B 36/008 166/250.1 |
| 2009/0312997 A1* | 12/2009 | Freed ..................... E21B 49/00 703/10 |
| 2010/0083748 A1* | 4/2010 | Kerr ....................... E21B 49/10 73/152.26 |
| 2012/0232799 A1 | 9/2012 | Zuo et al. |
| 2012/0232859 A1 | 9/2012 | Pomerantz et al. |
| 2012/0296617 A1* | 11/2012 | Zuo ........................ E21B 47/10 703/10 |
| 2013/0112406 A1 | 5/2013 | Zuo et al. |
| 2014/0200810 A1 | 7/2014 | Zuo et al. |

OTHER PUBLICATIONS

Burgess et al. "Formation Testing and Sampling through Casing", Oilfield Review, Spring 2002. pp. 46-57. (Year: 2002).*

* cited by examiner

(Prior Art)

ASPHALTENE GRADIENT MODELING METHODS

CROSS-REFERENCE TO RELATED APPLICATIONS

This application claims benefit of U.S. Provisional Patent Application Ser. No. 61/921,680, filed Dec. 30, 2013, which is herein incorporated by reference.

BACKGROUND OF THE DISCLOSURE

Modeling and simulation techniques have been developed for estimating the properties and/or behavior of petroleum fluid in a reservoir. Typically, these techniques employ an equation of state (EOS) model that represents the phase behavior of the petroleum fluid in the reservoir. Once the EOS model is defined, it can be used to assess reservoir connectivity and compartmentalization, as well as to compute a wide array of properties, such as volumetric factors and compressibility, heat capacity, saturation pressure (e.g. bubble point or dew point), and the density of each phase, among others. Downhole fluid analysis techniques can be employed to determine the composition of the petroleum fluid and this compositional data can be used as an input to develop the equation of state models. Asphaltenes are generally the heaviest fraction and the most polar component in a petroleum mixture and can behave differently (e.g., forming molecules, nanoaggregates, or clusters) depending on their concentration within the petroleum fluid. The Flory-Huggins Zuo Equation of State (FHZ EOS) can be employed to account for asphaltene gradients when modeling the phase behavior of petroleum fluid.

SUMMARY

The present disclosure relates to a modeling method that includes analyzing formation fluid within a fluid analyzer of a downhole tool at a plurality of stations to determine a change in a gas oil ratio with respect to depth. The method also includes employing the change in the gas oil ratio with respect to depth to determine a ratio of a solubility term and an entropy term to a gravity term. The method further includes developing an equation of state model based on the ratio.

The present disclosure also relates to a modeling method that includes analyzing formation fluid sampled from a plurality of depths within a wellbore to determine properties of the formation fluid. The method further includes employing the properties to determine a ratio of a solubility term and an entropy term to a gravity term and developing an equation of state model based on the ratio.

The present disclosure further relates to a downhole tool system that includes a fluid analyzer to determine properties of formation fluid. The system also includes a controller configured to execute instructions to determine a change in a gas oil ratio with respect to depth and calculate a ratio of a solubility term and an entropy term to a gravity term based on the determined changed in the gas oil ratio with respect to depth.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the present disclosure provides many different embodiments, or examples, for implementing different features of various embodiments. Specific examples of components and arrangements are described below to simplify the present disclosure. These are, of course, merely examples and are not intended to be limiting.

The present disclosure relates to methods for developing an equation of state (EOS) model for petroleum fluids having a relatively high gas oil ratio (GOR). According to certain embodiments, the EOS modeling techniques described herein may be employed for petroleum fluids having a GOR of greater than approximately 600-800 scf/STB, and all subranges therebetween, or more particularly, greater than approximately 700 scf/STB. The equation of state model is a simplified form of the FHZ EOS model, details of which are described in commonly assigned International Patent Application Publication No. WO 2012/042397, a copy of which is incorporated herein by reference in its entirety. The FHZ EOS model includes three types of terms: a gravity term that depends on the difference in densities between the asphaltenes and the bulk oil (e.g. the formation fluid mixture), a solubility term(s) that depends on the difference between the solubility parameters of the asphaltenes and the bulk oil, and an entropy term that depends on the change in volume of the bulk oil with respect to depth, accounting for the entropy of mixing. The simplified EOS model described herein for relatively high GOR fluids includes determining a ratio of the solubility and entropy terms to the gravity terms, allowing GOR data to be employed to develop the EOS model.

Figure 1:
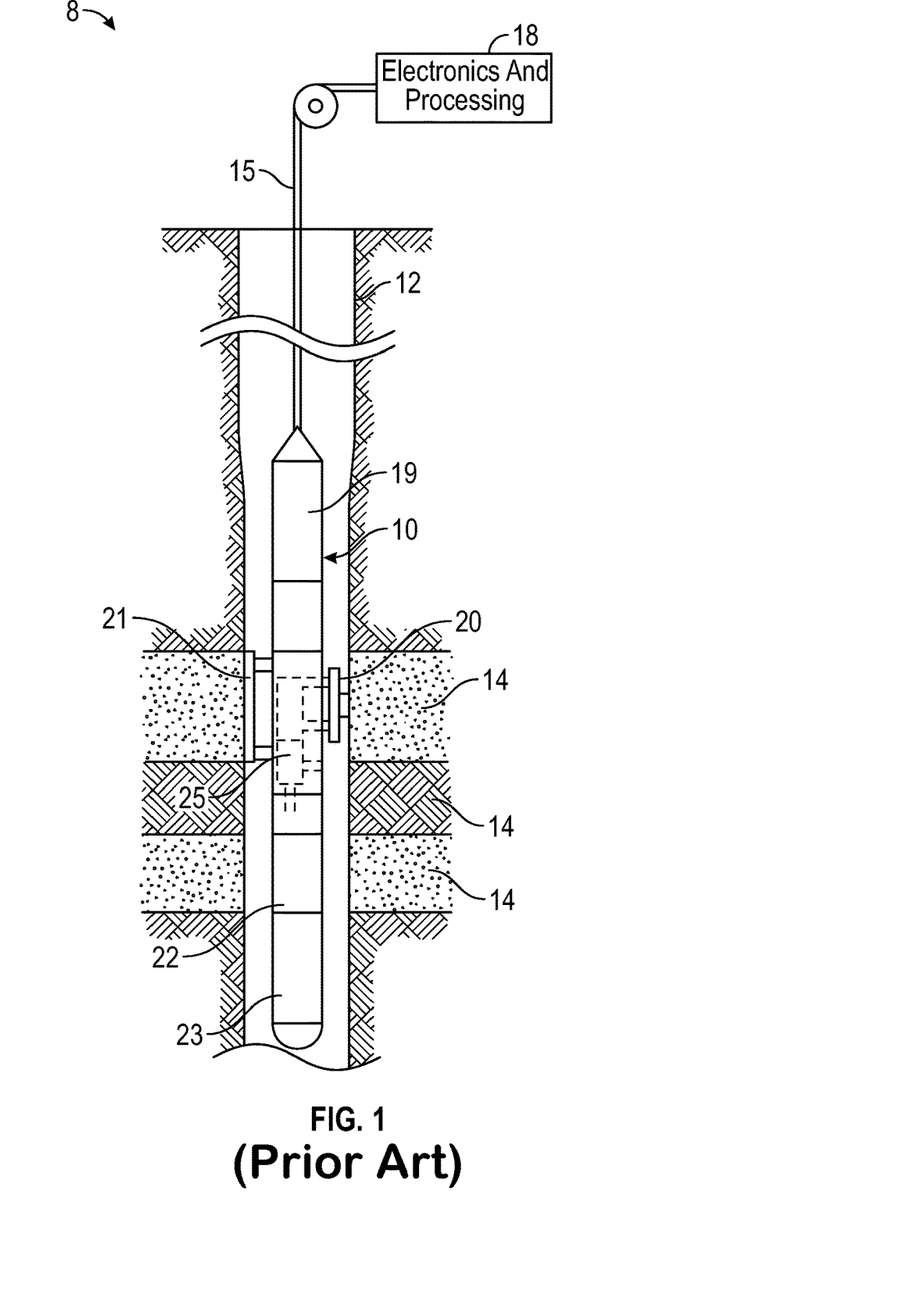
FIG. 1 is a schematic view of an embodiment of a downhole tool that may be used to develop an equation of state model, according to aspects of the present disclosure.

FIG. 1 depicts an example of a wellsite system 8 that may be employed to develop an equation of state model, according to the techniques described herein. The system 8 includes a downhole tool 10 suspended in a borehole 12 from the lower end of a multiconductor cable 15 that is spooled on a winch at the surface. The cable 15 is communicatively coupled to an electronics and processing system 18. The downhole tool 10 includes an elongated body 19 that carries a selectively extendable probe 20 and a selectively extendable tool anchor 21, which are respectively arranged on opposite sides of the body 19. The probe 20 is configured to selectively seal off or isolate selected portions of the wall of the borehole 12 to fluidly couple with the adjacent earth formation 14 and/or to draw fluid samples from the formation 14. The probe 20 may include a single inlet or multiple inlets designed for guarded or focused sampling. The formation fluid received through the probe 20 may be sent to through a flowline to a fluid analysis module 25. From the fluid analysis module 25, the formation fluid may be expelled to the borehole through a port in the body 19 or the formation fluid may be sent to one or more fluid sampling modules 22 and 23 through a flowline. The fluid sampling modules 22 and 23 may include sample chambers that store the formation fluid. In the illustrated example, the electronics and processing system 18 and/or a downhole control system are configured to control the extendable probe 20 and/or the drawing of a fluid sample from the formation 14.

As discussed further below with respect of FIG. 2, the fluid analysis module 25 includes components to measure the temperature and pressure of the fluid in the flowline. The fluid analysis module 25 also derives properties that characterize the formation fluid sample at the flowline pressure and temperature. In one embodiment, the fluid analysis module 25 measures absorption spectra and translates such measurements into concentrations of several alkane components and groups in the fluid sample. In an illustrative embodiment, the fluid analysis module 25 provides measurements of the concentrations (e.g., weight percentages) of carbon dioxide ($CO_2$), methane ($CH_4$), ethane ($C_2H_6$), the $C_3$-$C_5$ alkane group, the lump of hexane and heavier alkane components ($C_{6+}$), and asphaltene content. The fluid analysis module 25 measures live fluid density ($\rho$) at the flowline temperature and pressure, live fluid viscosity ($\mu$) at flowline temperature and pressure (in cP), formation pressure, and formation temperature.

Control of the probe 20, the fluid analysis module 25, and the flow path to the fluid sampling modules 22, 23 may be governed by the control system 18. As will be appreciated by those skilled in the art, the fluid analysis module 25 and the surface-located electronics and processing system 18 may include data processing functionality (e.g., one or more microprocessors, associated memory, and other hardware and/or software) to implement the methodology as described herein. The electronics and processing system 18 also may be realized by a distributed data processing system. The data measured by the downhole tool 10 may communicated (for example, in real time) over a communication link, e.g., a satellite link, to a remote location for data analysis, which can be carried out on a workstation or other suitable data processing system, e.g., a computer cluster or computing grid.

Formation fluids sampled by the downhole tool 10 may be contaminated with the mud filtrate of a drilling fluid that seeps into the formation 14 during the drilling process. In some examples, formation fluids are withdrawn from the formation 14 and pumped into the borehole or into a large waste chamber in the borehole tool 10 until the fluid being withdrawn becomes sufficiently clean. In a clean sample, the concentration of mud filtrate in the sample fluid is acceptably low so that the fluid substantially represents native (i.e., naturally occurring) formation fluids. In the illustrated example, the downhole tool 10 is provided with sample chambers disposed within the fluid sampling modules 22 and 23 to store collected fluid samples.

The system 8 of FIG. 1 makes in situ determinations regarding hydrocarbon bearing geological formations by downhole sampling of reservoir fluid at one or more measurement stations within the borehole 12 and conducts downhole fluid analysis (DFA) of one or more reservoir fluid samples for each measurement station (including compositional analysis, such as estimating concentrations of a plurality of compositional components of a given sample and other fluid properties). In accordance with a non-limiting example, the samples of gas condensates are collected from different depths. The downhole fluid analysis may be compared to an equation of state (EOS) model of the thermodynamic behavior of the fluid to characterize the reservoir fluid at different locations within the reservoir and determine fluid production parameters, transport properties, and other commercially useful indicators of the reservoir.

For example, the EOS model may provide a phase envelope that may be used to vary interactively the rate at which samples are collected and avoid entering the two-phase region. In another example, the EOS may assess production methodologies for the reservoir. Such properties may include density, viscosity, and volume of gas formed from a liquid after expansion to a specified temperature and pressure. The characterization of the fluid sample with respect to its thermodynamic model may also be used as a benchmark to determine the validity of the obtained sample, whether to retain the sample, and/or whether to obtain another sample at the location of interest. More particularly, based on the thermodynamic model and information regarding formation pressures, sampling pressures, and formation temperatures, if it is determined that the fluid sample was obtained near or below the bubble point of the sample, a decision may be made to discard the sample and/or to obtain a sample at a slower rate (i.e., a smaller pressure drop) so that gas will not evolve out of the sample. Because knowledge of the exact dew point of a retrograde gas condensate in a formation may be desirable, a decision may be made, when conditions allow, to vary the pressure drawdown in an attempt to observe the liquid condensation and thus establish the actual saturation pressure.

Figure 2:
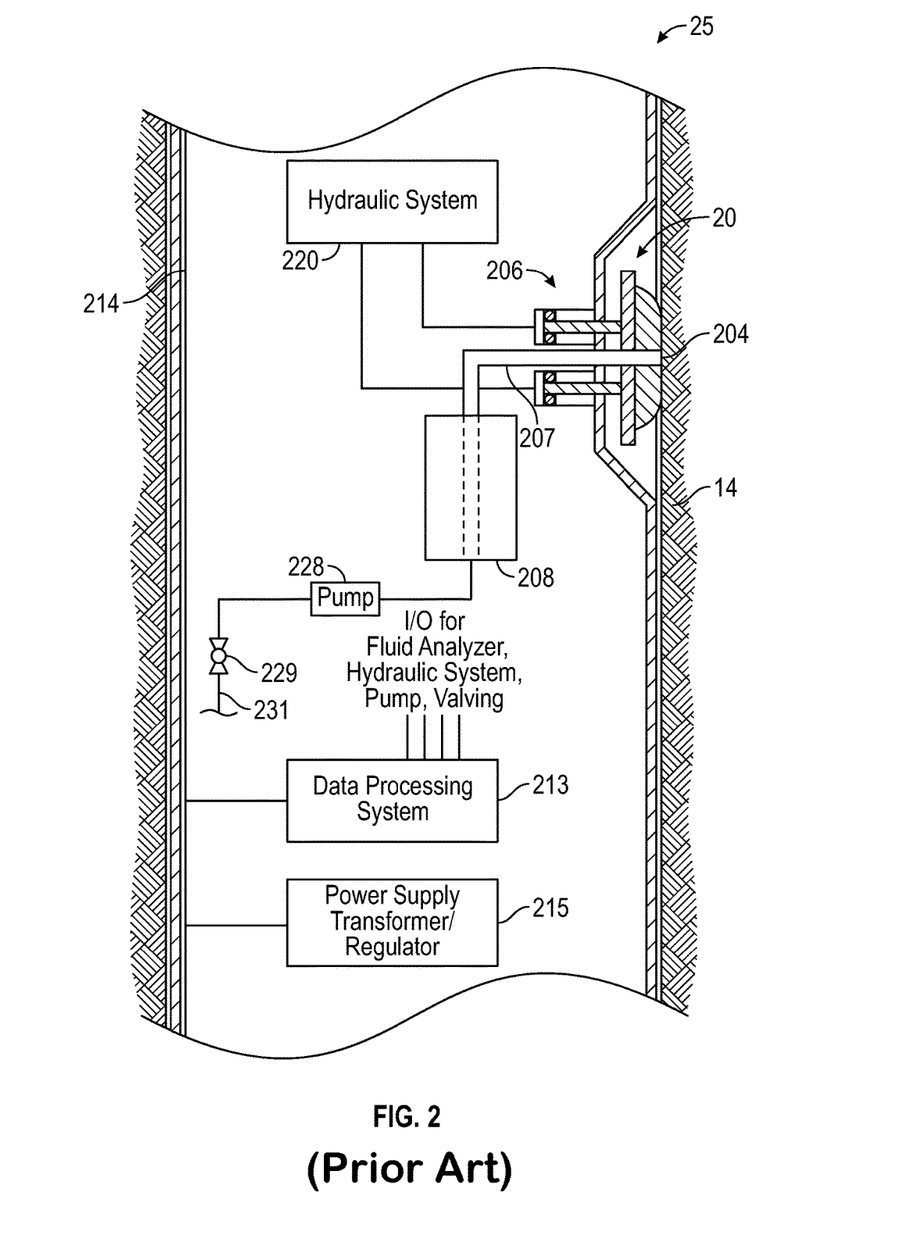
FIG. 2 is a schematic diagram of the fluid analysis module of the downhole tool of FIG. 1, according to aspects of the present disclosure.

FIG. 2 illustrates an embodiment of the fluid analysis module 25 of FIG. 1, including the probe 20, which has a port 204 to admit formation fluid therein. A hydraulic extending mechanism 206 may be driven by a hydraulic system 220 to extend the probe 202 to sealingly engage the formation 14. In other embodiments, more than one probe may be used to draw formation fluid into the downhole tool, or inflatable packers may replace the probe(s) and function to establish fluid connections with the formation and sample formation fluid, for example through an inlet disposed in the downhole tool between inflatable packers.

The fluid analysis module 25 includes a flowline 207 that carries formation fluid from the port 204 through a fluid analyzer 208. The fluid analyzer 208 may include a light source that directs light to a sapphire prism disposed adjacent to the flowline. The reflection of such light is analyzed by a gas refractometer and dual fluorescence detectors. The gas refractometer qualitatively identifies the fluid phase in the flowline. The dual fluorescence detectors detect free gas bubbles and retrograde liquid dropout to accurately detect single phase fluid flow in the flowline 207. Fluid type is also identified. The resulting phase information can be used to define the difference between retrograde condensates and volatile oils, which can have similar gas-oil ratios (GORs) and live-oil densities. It can also be used to monitor phase separation in real time and ensure single phase sampling. The fluid analyzer 208 also includes dual spectrometers—a filter array spectrometer and a grating-type spectrometer.

The filter array spectrometer of the fluid analyzer 208 includes a broadband light source providing broadband light that passes along optical guides and through an optical chamber in the flowline to an array of optical density detectors that are designed to detect narrow frequency bands (commonly referred to as channels) in the visible and near-infrared spectra, for example, as described in U.S. Pat. No. 4,994,671. The filter array spectrometer also employs optical filters that provide for identification of the color (also referred to as "optical density" or "OD") of the fluid in the flowline. Such color measurements support fluid identification, determination of asphaltene content and pH measurement. This grating type spectrometer of the fluid analyzer 208 is designed to detect channels in the near-infrared spectra (between 1600-1800 nm) where reservoir fluid has absorption characteristics that reflect molecular structure.

The fluid analyzer 208 also includes a pressure sensor for measuring pressure of the formation fluid in the flowline 207, a temperature sensor for measuring temperature of the formation fluid in the flowline 207, and a density sensor for measuring live fluid density of the fluid in the flowline 207. In addition to density, the density sensor can also provide a measurement of live fluid viscosity, for example, from the quality factor of oscillation frequency. Further, in certain embodiments, the fluid analyzer 208 also may measure the resistivity and pH of the fluid within the flowline. Moreover, the flowline sensors of the fluid analyzer 208 may be replaced or supplemented with other types of suitable measurement sensors (e.g., NMR sensors, capacitance sensors, etc.). Pressure sensor(s) and/or temperature sensor(s) for measuring pressure and temperature of fluid drawn into the flowline 207 can also be part of the probe 202.

The fluid analysis module 25 also includes a pump 228 that is fluidly coupled to the flowline 207. The pump may be controlled to draw formation fluid into the flowline 207 and supply the formation fluid to the fluid sampling modules 22 and 23 (FIG. 1A) via valve a 229 and a flowpath 231.

The fluid analysis module 25 includes a data processing system 213 that receives and transmits control and data signals to the other components of the module 25 for controlling operations of the fluid analysis module 25. The data processing system 213 also communicates with the fluid analyzer 208 for receiving, storing, and processing the measurement data generated therein. In one embodiment, the data processing system 213 processes the measurement data output by the fluid analyzer 208 to derive and store measurements of the hydrocarbon composition of fluid samples analyzed in situ by the fluid analyzer 208, including: flowline temperature; flowline pressure; live fluid density ($\rho$) at the flowline temperature and pressure; live fluid viscosity ($\mu$) at flowline temperature and pressure; concentrations (e.g., weight percentages) of carbon dioxide ($CO_2$), methane ($CH_4$), ethane ($C_2H_6$), the $C_3$-$C_5$ alkane group, the lump of hexane and heavier alkane components ($C_{6+}$), and asphaltene content; gas/oil ratio (GOR); and other parameters (such as API gravity, oil formation volume factor ($B_o$), etc.).

Flowline temperature and pressure is measured by the temperature sensor and pressure sensor, respectively, of the fluid analyzer 208 (and/or the probe 20). In one embodiment, the output of the temperature sensor(s) and pressure sensor(s) are monitored continuously before, during, and after sample acquisition to derive the temperature and pressure of the fluid in the flowline 207. Formation pressure can be measured by the pressure sensor of the fluid analyzer 208 in conjunction with the downhole fluid sampling and analysis at a particular measurement station after buildup of the flowline to formation pressure.

The GOR is determined by measuring the quantity of methane and liquid components of crude oil using near infrared absorption peaks. The ratio of the methane peak to the oil peak on a single phase live crude oil is directly related to GOR. The fluid analysis module 25 can also detect and/or measure other fluid properties of a live oil sample, including retrograde dew formation, asphaltene precipitation, and/or gas evolution.

The fluid analysis module 25 also includes a tool bus 214 that communicates data signals and control signals between the data processing system 213 and the electronics and processing system 18 of FIG. 1. The tool bus 214 can also carry electric power supply signals generated by a surface-located power source for supply to the fluid analysis module 25, and the module 25 can include a power supply transformer/regulator 215 for transforming the electric power supply signals supplied via the tool bus 214 to appropriate levels suitable for use by the electrical components of the module 25.

Although the components of FIG. 2 are shown and described above as being communicatively coupled and arranged in a particular configuration, persons of ordinary skill in the art will appreciate that the components of the fluid analysis module 25 can be communicatively coupled and/or arranged differently than depicted in FIG. 1B without departing from the scope of the present disclosure. In addition, the example methods, apparatus, and systems described herein are not limited to a particular conveyance type but, instead, may be implemented in connection with different conveyance types including, for example, coiled tubing, wireline, wired-drill-pipe, and/or other conveyance mechanisms known in the industry.

In accordance with the present disclosure, the system described above with respect to FIGS. 1 and 2 can be employed to develop an EOS model based on downhole fluid analysis (DFA) of samples of reservoir fluid. As will be appreciated by those skilled in the art, the surface-located electronics and processing system 18 and the fluid analysis module 25 of the downhole tool 10 each include data processing functionality (e.g., one or more microprocessors, associated memory, and other hardware and/or software) that cooperate to implement the method as described herein. The electronics and processing system 18 can also be realized by a distributed data processing system or workstation or other suitable data processing system (such as a computer cluster or computing grid).

Figure 3:
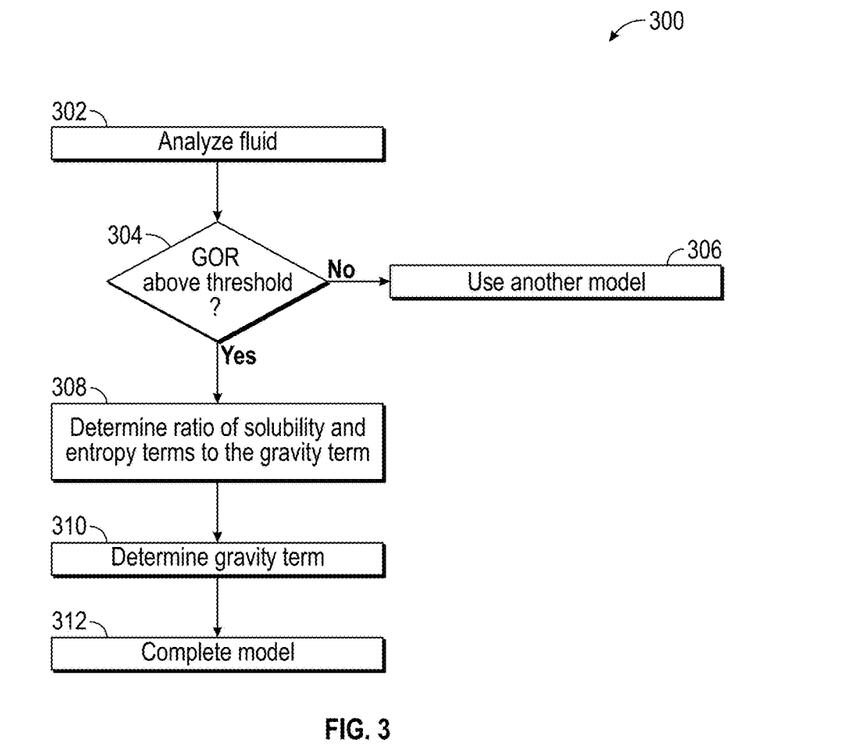
FIG. 3 is a flowchart depicting an embodiment of a method for developing an equation of state model, according to aspects of the present disclosure.

FIG. 3 is a flowchart depicting an embodiment of a method 300 that may be employed to develop an EOS model. The method 300 may begin by analyzing (block 302) the formation fluid at multiple depths within the borehole. For example, the formation fluid may be withdrawn into the downhole tool 10 through the probe 20 and analyzed within the fluid analyzer 208, as described above with respect to FIG. 2. The formation fluid may be withdrawn into the downhole tool 10 and analyzed while the downhole tool 10 is disposed at a first depth within the borehole to determine a first set of formation fluid properties, including composition, optical density, and GOR data, among others. The downhole tool 10 may then be moved within the borehole to a second depth, and formation fluid may again be withdrawn into the downhole tool 10 and analyzed while the downhole tool 10 is disposed at the second depth to determine a second set of formation fluid properties, including composition, optical density, and GOR data, among others. According to certain embodiments, one of the locations may be used as the reference depth, with the corresponding formation fluid measurements being employed as reference measurements.

In certain embodiments, the fluid analyzer 208 may measure the absorption spectra and translate the measurements into the concentrations of water ($H_2O$), carbon dioxide ($CO_2$), methane ($C_1$), ethane ($C_2H_6$), the $C_3$-$C_5$ alkane group including propane, butane, and pentane, and the lump of hexane and heavier alkane components ($C_{6+}$), among others. The fluid analyzer 208 may then employ the foregoing compositional information to determine the GOR, as well as additional fluid properties, such as the condensate yield, among others. In certain embodiments, the data processing system 213 may operate in conjunction with the fluid analyzer 208 to determine the GOR and additional fluid properties using the composition information received from the fluid analyzer 208. Additional details of fluid analysis techniques and methods that may be employed to analyze (block 302) the formation fluid are described in the following commonly assigned U.S. Pat. No. 8,434,356 to Hsu et al.; U.S. Pat. No. 7,920,970 to Zuo et al.; U.S. Pat. No. 7,822,554 to Zuo et al.; U.S. Pat. No. 7,526,953 to Goodwin et al.; U.S. Pat. No. 6,476,384 to Mullins et al; U.S. Pat. No. 5,331,156 to Hines et al.; and U.S. Pat. No. 4,994,671 to Safinya et al.; which are each herein incorporated by reference in their entirety.

The method may then continue by determining (block 304) whether the formation fluid has a relatively high GOR. For example, if the GOR determined using the fluid analyzer 208 is above a certain value, such as equal to or greater than approximately 500-1000 scf/STB, or more particularly, equal to or greater than approximately 700 scf/STB, the formation fluid may be determined to have a relatively high GOR. In certain embodiments, formation fluid measured at a single location may be employed to determine whether the formation fluid has a relatively high GOR, while in other embodiments, the GOR values from multiple locations within the borehole may be employed, for example, by taking the average or median, to determine whether the formation fluid has a relatively high GOR.

If the formation fluid does not have a relatively high GOR, another EOS model may be employed (block 306). For example, in certain embodiments, the full FHZ EOS model may be used, which as shown in Eq. 1 below treats the reservoir fluid as a mixture of two parts: a solute part (the high molecular weight fraction) and the oil mixture (or bulk reservoir fluid that includes the lower molecular weight fractions as well as the high molecular weight fraction). The solute part includes asphaltenes which depending on the concentration may exist as molecules (e.g., at low concentrations), as nanoaggregates (e.g., a medium concentrations), and as clusters of nanoaggregates (e.g., at high concentrations). In this approach, the relative concentration (volume fraction) of the asphaltene solute part as a function of depth is given by:

$$\frac{\phi_a(h_2)}{\phi_a(h_1)} = \frac{OD(h_2)}{OD(h_1)} = \exp\left\{\frac{v_a g(\rho_m - \rho_a)(h_2 - h_1)}{RT} + \left(\frac{v_a}{v_m}\right)_{h_2} - \left(\frac{v_a}{v_m}\right)_{h_1} - \frac{v_a[(\delta_a - \delta_m)^2_{h_2} - (\delta_a - \delta_m)^2_{h_1}]}{RT}\right\} \quad (1)$$

where $\phi_a(h_1)$ is the volume fraction for the solute part at depth $h_1$; $\phi_a(h_2)$ is the volume fraction for the solute part at depth $h_2$; $v_a$ is the partial molar volume for the solute part; $v_m$ is the molar volume for the oil mixture; $\delta_a$ is the solubility parameter for the solute part; $\delta_m$ is the solubility parameter for the oil mixture; $\rho_a$ is the partial density for the solute part; $\rho_m$ is the density for the oil mixture; R is the universal gas constant; g is the gravitational constant; T is the absolute temperature of the reservoir fluid; $OD(h_1)$ is the optical density at depth $h_1$; and $OD(h_2)$ is the optical density at depth $h_2$.

In Eq. 1 it is assumed that properties of the solute part (e.g., the high molecular weight fraction) are independent of depth. For properties of the oil mixture that are a function of depth, average values between depths can be used. The first exponential term of Eq. 1 arises from gravitational contributions. The second and third exponential terms arise from the combinatorial entropy change of mixing. The fourth exponential term rises from the enthalpy (solubility) change of mixing. It can be assumed that the reservoir fluid is isothermal. In this case, the temperature T can be set to the average formation temperature as determined from downhole fluid analysis. Alternatively, a temperature gradient with depth (preferably a linear temperature distribution) can be derived from downhole fluid analysis and the temperature T at a particular depth determined from such temperature gradient. A detailed description of the full FHZ EOS can be found in commonly owned U.S. patent application Ser. No. 13/382,549, Publication No. 2012/0296617, which is incorporated herein by reference in its entirety.

For relatively low GOR fluids, such as those with a GOR below approximately 500-1000 scf/STB, or more specifically below 700 scf/STB, the full FHZ EOS may be simplified to include only the gravitational term, with the entropy and enthalpy terms cancelling out, as shown below:

$$\frac{\phi_i(h_2)}{\phi_i(h_1)} = \frac{OD(h_2)}{OD(h_1)} = \exp\left(\frac{v_a g(\rho_m - \rho_a)(h_2 - h_1)}{RT}\right) \quad (2)$$

A detailed description of Eq. (2) can be found in commonly owned U.S. patent application Ser. No. 12/483,813, Publication No. 2009/0312997, which is incorporated herein by reference in its entirety.

If the fluid has a relatively high GOR, for example, equal to or greater than approximately 700 scf/STB, a simplified form of the FHZ EOS may be employed that uses a ratio of the entropy and solubility (enthalpy) terms to the gravity term. The simplified form of the FHZ EOS for relatively high GOR fluids is shown as follows:

$$\frac{\phi_i(h_2)}{\phi_i(h_1)} = \frac{OD(h_2)}{OD(h_1)} = \exp\left\{\frac{v_a g(\rho_m - \rho_a)(h_2 - h_1)}{RT}\left(1 + R_{\frac{SOL+ENT}{GRAV}}\right)\right\} \quad (3)$$

where $$R_{\frac{SOL+ENT}{GRAV}}$$

is the ratio of entropy terms (e.g., the second and third exponential terms of Eq. 1) and the enthalpy (e.g., the fourth exponential solubility term of Eq. 1) and to the gravity term (e.g., the first exponential term of Eq. 1).

This ratio can be approximated by the following expression:

$$R_{\frac{SOL+ENT}{GRAV}} = \frac{SOL}{GRAV} + \frac{ENT}{GRAV} = -A\frac{\partial \phi_{C1}}{\partial h} + \frac{kTB}{g(\rho_a - \rho_m)}\frac{\partial \phi_{C1}}{\partial h} \quad (4)$$

where A and B are constants given by A=−28000 m and B=−8 $nm^{-3}$; k is the Boltzmann constant; $\phi_{C1}$ is the volume fraction of the methane; SOL/GRAV is the ratio of the enthalpy (solubility) term to the gravity term and ENT/

GRAY is the ratio of the entropy term to the gravity term. The values of the constants A and B may generally apply to a wide variety of oils; however, in certain embodiments, the values of A and B may vary by approximately 1-5%, and all subranges therebetween, or other values of A and B may be employed, depending on the specific type of oil. Further, where the units of the other terms vary, the values of A and B may change. For example, where $\phi_{C1}$ is the volume percentage of the methane, the values of A and B may be given by A=−280 m and B=−0.08 nm$^{-3}$.

Once the fluid is determined to be a relatively high GOR fluid, the method 300 may continue by determining (block 308) the ratio of the solubility and entropy terms to the gravity term, as shown in Eq. 4. Three different techniques may be employed to determine the ratio of Eq. 4.

The first technique calculates the derivative of the volume fraction of methane with respect to depth according to the following Eq. 5:

$$\frac{\partial \phi_{C1}}{\partial h} \approx \frac{\phi_{C1}(h_2) - \phi_{C2}(h_1)}{h_2 - h_1} \quad (5)$$

where $\phi_{C1}(h_1)$ is the volume fraction of methane at depth $h_1$; and $\phi_{C2}(h_2)$ is the volume fraction of methane at depth $h_2$. The terms $\phi_{C1}(h_1)$ and $\phi_{C2}(h_2)$ may be determined using the compositional information obtained from the fluid analysis measurements (block 202) made at depths $h_1$ and $h_2$. In certain embodiments, the volume fractions of methane may be approximated using the weight fractions of methane obtained from the compositional information.

The second techniques calculates the derivative of the volume fraction of methane with respect to depth according to the following Eq. 6:

$$\frac{\partial \phi_{C1}}{\partial h} \approx \frac{a}{(1 + bGOR)^2} \frac{\partial GOR}{\partial h} \quad (6)$$

where a and b are constants given by a=0.0355(scf/stb)$^{-1}$ and b=4.23×10$^{-4}$ (scf/stb)$^{-1}$; and GOR represents the average of the GOR at depth $h_1$ and the GOR at depth $h_2$. The derivative of the GOR with respect to depth can be calculated according to the following Eq. 7:

$$\frac{\partial GOR}{\partial h} \approx \frac{(GOR(h_2) - GOR(h_1))}{h_2 - h_1} \quad (7)$$

where GOR($h_2$) represents the GOR of the fluid at depth $h_2$ and GOR($h_1$) represents the GOR of the fluid at depth $h_1$, both of which can be determined from the fluid analysis measurements made using the fluid analyzer (block 302).

The derivative of the volume fraction of methane with respect to depth, calculated using the first or second technique, can then be employed in Eq. 4 to determine the ratio of the solubility and entropy terms to the gravity term. The remaining terms in Eq. 4 are either constants or values that can be determined from the fluid analysis measurements (block 302). For example, as noted above, A is a constant represented by the value of approximately −28000 m; g is the gravitational constant; R is the universal gas constant; and T is the absolute temperature of the reservoir fluid. The temperature of the fluid can be averaged for depths $h_1$ and $h_2$ or one of the temperature measurements from $h_1$ or $h_2$ can be employed. The density $\rho_m$ of the oil mixture at one or more depths can also be measured by downhole fluid analysis and the measurements for depths $h_1$ and $h_2$ can be averaged or one of the density measurements from $h_1$ or $h_2$ can be employed. The standard value of 1.2 g/cc can be used for the density $\rho_a$ of the solute asphaltene part.

Rather than calculating the derivative of the volume fraction of methane with respect to depth (e.g., height), a third technique employs charts to determine the ratio of Eq. 4. In certain embodiments, the charts may be stored in algorithmic form in a memory or other tangible readable medium of the data processing system 213 and/or the electronics and processing system 18. Moreover, in yet other embodiments, the charts may be employed by an operator at the surface and the resulting values may be input into the electronics and processing system 18 at the surface.

Figure 4:
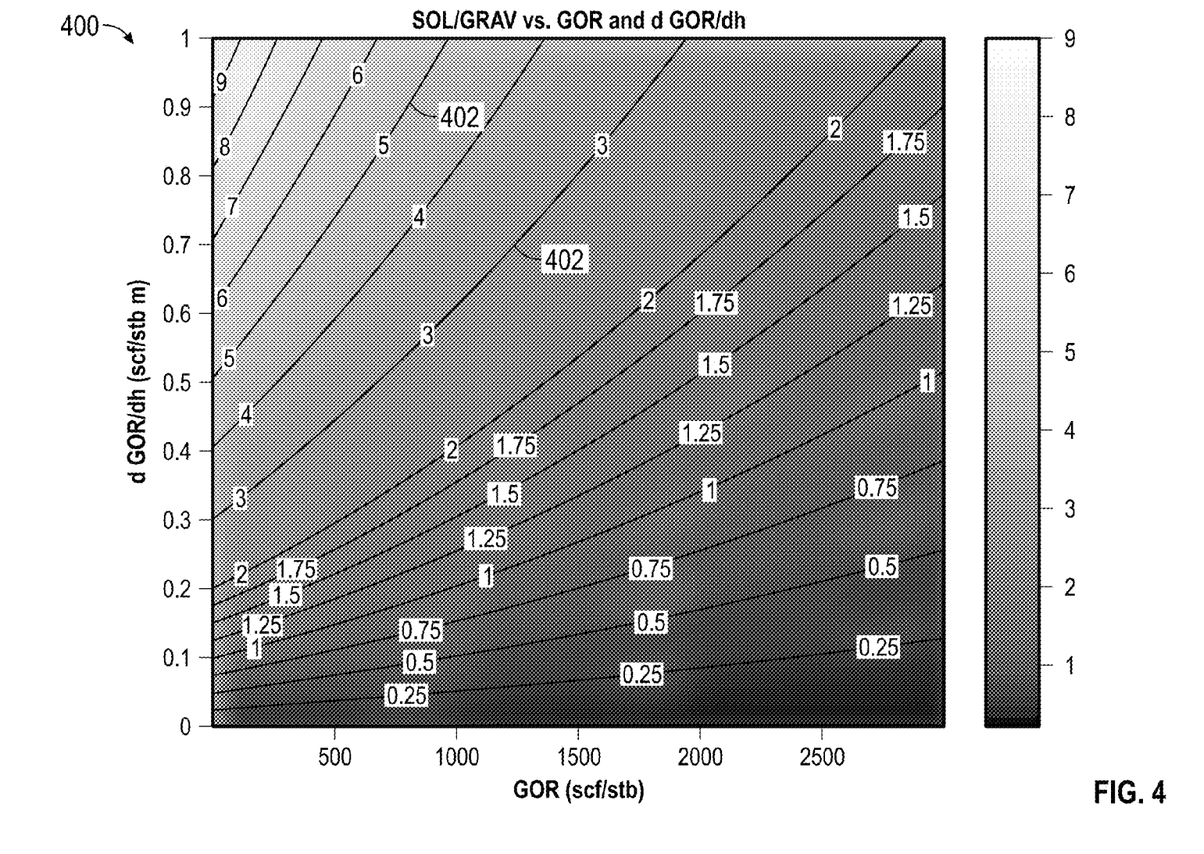
FIG. 4 is a chart depicting an embodiment of a relationship between gas oil ratio and an equation of state modeling terms, according to aspects of the present disclosure.

In the third technique, the ratio SOL/GRAV may be determined using a chart, an embodiment of which is shown in FIG. 4. The chart 400 depicts the GOR on the x-axis and the derivative of the GOR with respect to depth on the y-axis. Curves 402 show the ratios that correspond to certain values of the GOR and change in GOR with respect to depth. The GORs measured at depths $h_1$ and $h_2$ can be used to determine the x and y axis values and the resulting ratio can be determined, ranging from 0 to 9. According to certain embodiments, the chart 400 may be developed based on historical fluid analysis data and/or correlations between the solubility parameters and density.

Also in the third technique, the ratio ENT/GRAV can be calculated from the equation:

$$N = \frac{ENT}{GRAV} \frac{g(\rho_a - \rho_m)}{kT} \quad (8)$$

Figure 5:
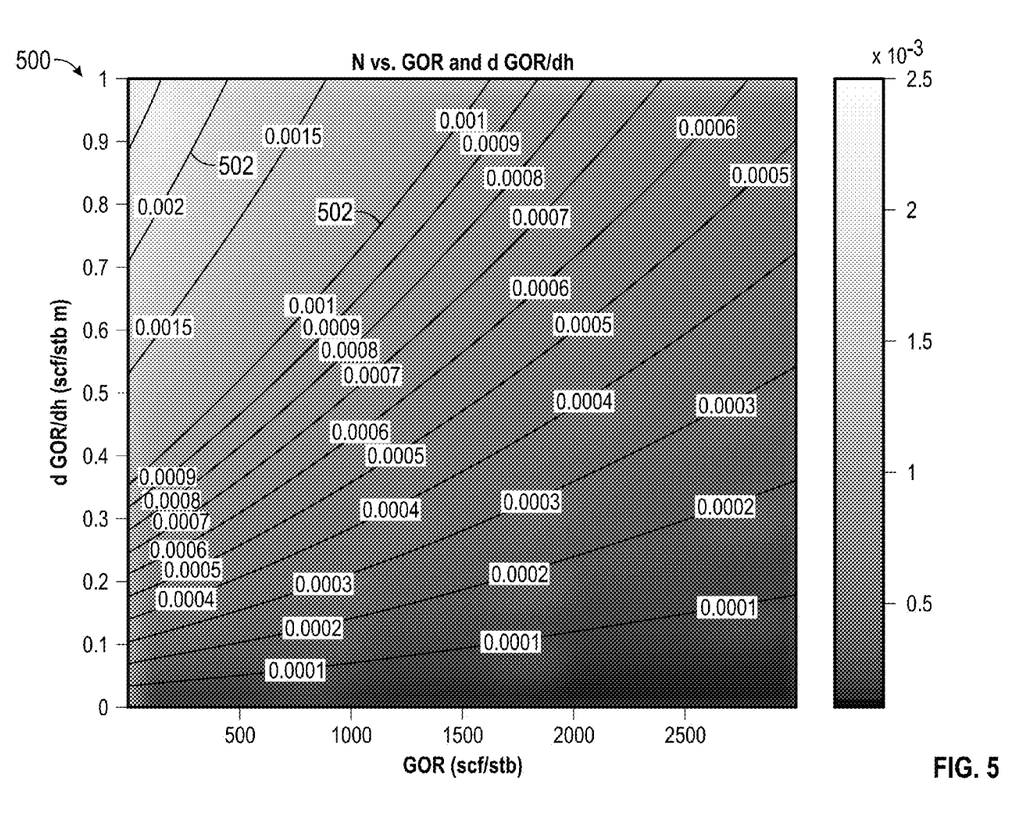
FIG. 5 is a chart depicting another embodiment of a relationship between gas oil ratio and an equation of state modeling terms, according to aspects of the present disclosure.

The value of N can be obtained using a chart, an embodiment of which is shown in FIG. 5. The chart 500 depicts the GOR on the x-axis and the derivative of the GOR with respect to depth on the y-axis. Curves 502 show the N values that correspond to certain values of the GOR and change in GOR with respect to depth. The GORs measured at depths $h_1$ and $h_2$ can be used to determine the x and y axis values and the resulting value of 9 can be determined, ranging from 0 to 2.5×10$^3$. Once the value of N is obtained, the ratio $$\frac{ENT}{GRAV}$$

can be found by multiplying N by $$\frac{kT}{g(\rho_a - \rho_m)},$$

where as noted above, g is the gravitational constant; k is the Boltzmann constant; and T is the absolute temperature of the reservoir fluid. The temperature of the fluid can be averaged for depths $h_1$ and $h_2$ or one of the temperature measurements from $h_1$ or $h_2$ can be employed. The density $\rho_m$ of the oil mixture at one or more depths can also be measured by downhole fluid analysis and the measurements for depths $h_1$ and $h_2$ can be averaged or one of the density measurements from $h_1$ or $h_2$ can be employed. The standard value of 1.2 g/cc can be used for the density $\rho_a$ of the solute asphaltene part. The ratio $R_{\frac{SOL+ENT}{GRAV}}$ is then given by:

$$R_{\frac{SOL+ENT}{GRAV}} = \frac{SOL}{GRAV} + N\frac{kT}{g(\rho_a - \rho_m)} \qquad (9)$$

where g has units of m/s², and ρ has units of g/cm³. According to certain embodiments, the chart 500 may be developed based on historical fluid analysis data and/or correlations between molar volumes and methane concentrations.

Once the ratio of the enthalpy and entropy terms to the gravity term has been determined (block 308), the gravity term can be determined (block 310) using the constants and values obtained from the fluid analysis, as described above. For example, the temperature T, the molar volume $v_a$, and the density $\rho_m$ of the oil mixture can be measured by downhole fluid analysis. Further, in certain embodiments, the molar volume may be determined by using additional equation of state models. The difference in depth can also be measured, while constants can be employed for the remaining terms. The gravitational term and the ratio of the enthalpy and entropy terms to the gravitational term can then be combined to complete the EOS model of Eq. 4.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method comprising:
   taking a plurality of samples of formation fluid, via a downhole tool, at a plurality of stations;
   analyzing the formation fluid within a fluid analyzer of the downhole tool at the plurality of stations to determine a change in a gas oil ratio with respect to depth;
   employing the change in the gas oil ratio with respect to depth to determine a ratio of a solubility term (SOL) and an entropy term (ENT) to a gravity term (GRAV), represented by a formula:

$$R_{\frac{SOL+ENT}{GRAV}} = \frac{SOL}{GRAV} + \frac{ENT}{GRAV};$$

developing an equation of state model based on the ratio; and
   applying the developed equation of state model in a production or exploration of the formation fluid.

2. The method of claim 1, wherein analyzing the formation fluid comprises measuring an absorption spectra of the formation fluid.

3. The method of claim 1, wherein analyzing the formation fluid comprises determining a first gas oil ratio at a first depth within a wellbore and determining a second gas oil ratio at a second depth within the wellbore.

4. The method of claim 1, wherein analyzing the formation fluid comprises determining concentrations of carbon components within the formation fluid.

5. The method of claim 1, wherein employing the change comprises determining a first ratio of the solubility term to the gravity term and a second ratio of the entropy term to the gravity term.

6. The method of claim 1, wherein the equation of state model represents a change in solute concentration with respect to depth.

7. The method of claim 1, wherein the ratio is represented by an equation:

$$R_{\frac{SOL+ENT}{GRAV}} = -A\frac{\partial \phi_{C1}}{\partial h} + \frac{kTB}{g(\rho_a - \rho_m)}\frac{\partial \phi_{C1}}{\partial h}$$

where k represents the Boltzmann constant; $\phi_{c1}$ represents a volume fraction of methane in the formation fluid; g represents the gravitational constant; T represents a temperature of the formation fluid; $\rho_a$ represents a partial density of asphaltenes in the formation fluid; $\rho_m$ represents density of the formation fluid; and A and B are constants determined based on the type of formation fluid.

8. The method of claim 1, wherein applying the developed equation of state model in a production or exploration of the formation fluid comprises:
   determining a rate at which samples are to be collected to avoid entering a two-phase state of the formation fluid based at least in part on the equation of state model; and
   taking an additional sample at the determined rate via the downhole tool.

9. A method comprising:
   analyzing formation fluid sampled from a plurality of depths within a wellbore to determine properties of the formation fluid;
   employing the properties to determine a ratio of a solubility term (SOL) and an entropy (ENT) term to a gravity term (GRAV), represented by a formula:

$$R_{\frac{SOL+ENT}{GRAV}} = \frac{SOL}{GRAV} + \frac{ENT}{GRAV};$$

developing an equation of state model based on the ratio; and
   applying the developed equation of state model in a production or exploration of the formation fluid.

10. The method of claim 9, wherein employing the properties comprises determining a change in a volume fraction of methane with respect to depth.

11. The method of claim 9, wherein analyzing the formation fluid comprises analyzing a first sample of the formation fluid taken at a first depth, analyzing a second sample of the formation fluid taken at a second depth, and determining a weight fraction of methane in the first sample and the second sample.

12. The method of claim 9, wherein employing the properties comprises determining a change in a gas oil ratio with respect to depth.

13. The method of claim 9, wherein the equation of state model represents a change in asphaltene concentration with respect to depth.

14. The method of claim 9, wherein the gravity term comprises:

$$\left( \frac{v_a g (\rho_m - \rho_a)(h_2 - h_1)}{RT} \right)$$

where $v_a$ represents a partial molar volume of asphaltenes in the formation fluid; $h_1$ represents a first depth of the plurality of depths; $h_2$ represents a second depth of the plurality of depths; $\rho_a$ represents a partial density of the asphaltenes in the formation fluid; $\rho_m$ represents a total density of the formation fluid; R is the universal gas constant; g is the gravitational constant; and T represents temperature of the formation fluid.

15. The method of claim 9, wherein the solubility term comprises:

$$\left\{ \left( \frac{v_a}{v_m} \right)_{h_2} - \left( \frac{v_a}{v_m} \right)_{h_1} \right\}$$

where $v_a$ represents a partial molar volume of asphaltenes in the formation fluid; where $v_m$ represents a total molar volume of the formation fluid $h_1$ represents a first depth of the plurality of depths; and $h_2$ represents a second depth of the plurality of depths.

16. The method of claim 9, wherein the entropy term comprises:

$$\left\{ \frac{v_a \left[ (\delta_a - \delta_m)^2_{h_2} (\delta_a - \delta_m)^2_{h_1} \right]}{RT} \right\}$$

where $V_a$ represents a partial molar volume of asphaltenes in the formation fluid; $\delta_a$ represents a solubility parameter for the asphaltenes; $\delta m$ represents a solubility parameter for the formation fluid; $h_1$ represents a first depth of the plurality of depths; $h_2$ represents a second depth of the plurality of depths; R is the universal gas constant; g is the gravitational constant; and T represents temperature of the formation fluid.

17. A downhole tool system comprising:
   a fluid analyzer to determine properties of formation fluid; and
   a controller configured to execute instructions to:
      determine a change in a gas oil ratio with respect to depth;
      calculate a ratio of a solubility term and an entropy term to a gravity term based on the determined change in the gas oil ratio with respect to depth, wherein the ratio of the solubility term (SOL) and the entropy term (ENT) to the gravity term (GRAV) is represented by a formula:

$$R_{\frac{SOL+ENT}{GRAV}} = \frac{SOL}{GRAV} + \frac{ENT}{GRAV};$$

and
      generate an equation of state of the formation fluid corresponding to one or more depths of a formation based at least in part on the ratio.

18. The system of claim 17, wherein the instructions are stored within the downhole tool.

19. The system of claim 17, wherein the fluid analyzer comprises an optical spectrometer, or a gas chromatograph, or both.

20. The system of claim 17, comprising an extendable probe configured to direct the formation fluid into the fluid analyzer.

* * * * *